(12) United States Patent
Kauphusman et al.

(10) Patent No.: US 9,717,501 B2
(45) Date of Patent: *Aug. 1, 2017

(54) METHODS AND SYSTEMS FOR OCCLUDING VESSELS DURING CARDIAC ABLATION INCLUDING OPTIONAL ELECTROANATOMICAL GUIDANCE

(75) Inventors: James V. Kauphusman, Champlin, MN (US); Andre d'Avila, Florianopolis (BR); Vivek Y. Reddy, New York City, NY (US); William M. Sutton, Minnetonka, MN (US); Steven C. Christian, New Brighton, MN (US); Harry A. Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1426 days.

This patent is subject to a terminal disclaimer.

(21) Appl. No.: 12/785,227

(22) Filed: May 21, 2010

(65) Prior Publication Data

US 2010/0324552 A1 Dec. 23, 2010

Related U.S. Application Data

(63) Continuation-in-part of application No. PCT/US2008/084406, filed on Nov. 21, 2008.
(Continued)

(51) Int. Cl.
*A61B 18/12* (2006.01)
*A61B 17/12* (2006.01)
(Continued)

(52) U.S. Cl.
CPC .... *A61B 17/12036* (2013.01); *A61B 17/1204* (2013.01); *A61B 17/12109* (2013.01);
(Continued)

(58) Field of Classification Search
CPC .......... A61B 17/12036; A61B 17/1204; A61B 17/12109; A61B 17/12122;
(Continued)

(56) References Cited

U.S. PATENT DOCUMENTS 5,090,958 A * 2/1992 Sahota ...................... 604/98.01
5,417,689 A 5/1995 Fine
(Continued)

*Primary Examiner* — Michael Peffley
*Assistant Examiner* — Khadijeh Vahdat
(74) *Attorney, Agent, or Firm* — Dykema Gossett PLLC

(57) ABSTRACT

A method is provided for ablating a portion of the myocardium. The method includes inserting an occlusion catheter into a vessel on a heart, occluding the vessel using the occlusion catheter, inserting an ablation catheter into a chamber of the heart, positioning the ablation catheter against the myocardium, and ablating a portion of the myocardium while the vessel is occluded. The system includes an occlusion catheter having a catheter body including a tubular member having a distal portion and a bend located in the distal portion, a balloon located proximal of the bend and configured to contact an inner surface of the CS when positioned therewithin, a plurality of marker bands positioned on the catheter body, and a plurality of electrodes positioned on the catheter body. One or more electrodes or coils can be used as a reference for an electroanatomical system and can be disposed on the occlusion catheter.

10 Claims, 9 Drawing Sheets

Related U.S. Application Data

(60) Provisional application No. 60/989,807, filed on Nov. 21, 2007, provisional application No. 61/232,260, filed on Aug. 7, 2009.

(51) Int. Cl.
    *A61B 18/14* (2006.01)
    *A61B 18/00* (2006.01)

(52) U.S. Cl.
    CPC .. *A61B 17/12122* (2013.01); *A61B 17/12136* (2013.01); *A61B 18/1492* (2013.01); *A61B 2018/00214* (2013.01); *A61B 2018/00285* (2013.01); *A61B 2018/00577* (2013.01); *A61B 2018/00797* (2013.01); *A61B 2018/00815* (2013.01); *A61B 2018/00821* (2013.01)

(58) Field of Classification Search
    CPC ............ A61B 17/12136; A61B 18/14; A61B 18/1492; A61B 2018/00214; A61B 2018/00285; A61B 2018/00577; A61B 2018/00797; A61B 2018/00815; A61B 2018/00821
    USPC .................. 606/41; 600/374, 424
    See application file for complete search history.

(56) References Cited

U.S. PATENT DOCUMENTS

| | | | |
|---|---|---|---|
| 5,540,679 A * | 7/1996 | Fram et al. | 606/27 |
| 5,735,290 A | 4/1998 | Sterman et al. | |
| 5,738,652 A | 4/1998 | Boyd et al. | |
| 5,775,327 A * | 7/1998 | Randolph et al. | 600/374 |
| 2001/0021849 A1 | 9/2001 | Swartz et al. | |
| 2002/0010419 A1 * | 1/2002 | Jayaraman | 604/103.02 |
| 2002/0013548 A1 * | 1/2002 | Hinchliffe | 604/101.01 |
| 2002/0026182 A1 * | 2/2002 | Joye et al. | 606/21 |
| 2002/0038120 A1 * | 3/2002 | Duhaylongsod et al. | 606/15 |
| 2002/0042611 A1 | 4/2002 | Sliwa et al. | |
| 2002/0087156 A1 * | 7/2002 | Maguire et al. | 606/41 |
| 2002/0183730 A1 | 12/2002 | Reu et al. | |
| 2005/0059883 A1 * | 3/2005 | Peterson | A61B 17/34 600/424 |
| 2005/0065504 A1 * | 3/2005 | Melsky et al. | 606/16 |
| 2006/0058775 A1 * | 3/2006 | Stevens et al. | 604/509 |
| 2006/0276710 A1 * | 12/2006 | Krishnan | 600/424 |
| 2007/0129720 A1 * | 6/2007 | Demarais et al. | 606/41 |
| 2008/0249463 A1 * | 10/2008 | Pappone et al. | 604/101.05 |

\* cited by examiner

METHODS AND SYSTEMS FOR OCCLUDING VESSELS DURING CARDIAC ABLATION INCLUDING OPTIONAL ELECTROANATOMICAL GUIDANCE

CROSS REFERENCE TO RELATED APPLICATIONS

This application is a continuation-in-part of international patent application no. PCT/US2008/084406 filed 21 Nov. 2008 (the '406 application) which in turn claims the benefit of U.S. provisional application No. 60/989,807 filed 21 Nov. 2007, (the '807 application), and the instant application furthermore claims the benefit of U.S. provisional patent application No. 61/232,260 filed 7 Aug. 2009 (the '260 application). The '406, the '807, and the '260 applications are hereby incorporated by reference as though fully set forth herein. The instant application is also related to non-provisional U.S. patent application Ser. No. 12/785,140, filed 21 May 2010, now U.S. Pat. No. 9,572,583, the contents of which are also fully incorporated herein.

BACKGROUND OF THE INVENTION a. Field of the Invention

The field of the invention relates generally to cardiac ablation, and, more particularly, to vascular occlusion during cardiac ablation procedures including optional electroanatomical guidance during said procedures.

b. Description of Related Art

Atrial fibrillation is a form of arrhythmia and results from disorganized electrical activity in the heart muscle, or myocardium. As a result of abnormalities in the heart's electrical activity, the heart does not beat effectively and it is not able to pump the blood out properly.

Ablation of the mitral isthmus, defined as a narrow region between the mitral annulus and the left inferior pulmonary vein ostium, appears to increase the success rate of treating chronic atrial fibrillation. However, it is difficult to create transmural lesions in this region, even though the myocardial thickness in the mitral isthmus is not particularly greater than in other regions of the left atrium. Incomplete or non-continuous lesions and/or unidirectional mitral isthmus block can be problematic as it may result in recurrence of arrhythmia and/or a proarrhythmic effect by slowing conduction through the mitral isthmus. High-power endocardial ablations, as well as delivery of radio frequency (RF) energy into the coronary sinus (CS) and the great cardiac vein (epicardial portion of the mitral isthmus), are frequently used to prevent incomplete lines. This combined epicardial/endocardial approach sometimes allows for bidirectional isthmus block to be achieved but includes certain risks and complexities relating to anatomy near the mitral isthmus and the effects of blood flowing through the CS also near the mitral isthmus.

BRIEF DESCRIPTION OF THE INVENTION

In one aspect, an inventive method is provided for ablating a portion of the myocardium. The method includes inserting an inventive occlusion catheter into a vessel on a heart, occluding the vessel using the occlusion catheter, inserting an ablation catheter into a chamber of the heart, positioning the ablation catheter against the myocardium, and ablating a portion of the myocardium while the vessel is occluded. The occlusion catheter includes electrodes which can be used for visualization (e.g., via fluoroscopy, impedance- or magnetic-based electroanatomical visualization and location systems, and the like).

In another aspect, a method is provided for ablating a portion of the atrial myocardium. The method includes inserting a balloon catheter into a CS, inserting an ablation catheter into a left atrium of a heart, and ablating a portion of the atrial myocardium while a balloon, or expandable film of material or the like (herein "balloon") on the balloon catheter is expanded.

In a further aspect, an occlusion catheter is provided that includes a catheter body including a tubular member having a distal portion and a bend located in the distal portion. The occlusion catheter also includes a balloon located proximal of the bend and configured to contact an inner surface of the CS when positioned therewithin. A plurality of marker bands are positioned on the catheter body and a plurality of electrodes and/or metallic coils also are positioned on the catheter body to promote fluoroscopic visualization and localization and visualization via an electroanatomical system, respectively. The bend can promote anchoring of the occlusion catheter in a desired position relative to the os of the CS. A selectable one of the plurality of active electrodes and/or metallic coils can be selected as a reference node for an impedance- or magnetic-based electroanatomical system, respectively. That is, at least one of orientation, location and position of can be determined for other catheters, such as ablation catheters, relative to the reference node. If the other catheter(s) include at least three electrodes or coils (e.g., tip- or ring-type electrodes, metallic coils and the like) and the type of catheter and spacing of the elements is known the catheter can be simulated in the context of a 3D geometry generated by a roving catheter. The shaft of the catheter having the selected reference node can be simulated in vivo as well as various mapping and therapy delivery and sensing/imaging catheters, if desired. The spacing between active elements, such as electrodes provides relative spatial reference information and allows the 3D geometry of an organ, such as a heart, to have dimensions scaled to the actual dimensions.

Accordingly, the present disclosure provides devices and methods for anchoring a reference electrode or a magnetic coil or the like for use, for example, in an electroanatomical myocardial mapping or ablation procedure. The present disclosure also provides devices and methods for anchoring a reference electrode within a vessel while preserving a degree of perfusion through the vessel, if desired. Another aspect of the present disclosure provides devices and methods to anchor an electrode within a vessel for use in diagnostic and/or therapeutic procedures.

Thus, herein described, depicted, and claimed are catheters for anchoring an electrode in a portion of a CS, such as a portion of the great vein stemming therefrom. Such a catheter can include: an elongate catheter body adapted to be inserted into a portion of a vessel coupled to the CS and/or the great cardiac vein, the elongate catheter body including an anchor section having an expandable axial cross-section; at least one marker band or electrode disposed on the catheter body; and an actuation mechanism operably coupled to the anchor section to actuate the anchor section between an undeployed configuration, wherein the expandable axial cross-section of the anchor section is in a collapsed or unbent state, and a deployed configuration, wherein the anchor section is in an expanded or bent state. When the anchor section is in the deployed configuration, for example, an expandable axial cross-section can engage a tissue surface of the CS to inhibit movement between the catheter body and the CS without necessarily completely occluding the CS such that the at least one electrode or marker band remain in a stable, or reference, position. The at least one electrode or marker band may be positioned distally of the anchor section, proximally of the anchor section, in an essentially linear array, and/or on or as a minor part of the anchor section.

In some embodiments, the catheter body includes at least one perfusion passage having a first opening positioned distally of the anchor section and a second opening positioned proximally of the anchor section. This permits a degree of perfusion through the interior of the catheter body, if desired. Alternatively, or in addition, the catheter may be configured so that the degree of perfusion occurs through the vessel around the exterior of the catheter body and/or cause the distal tip to bend or deflect. Thus, for a medical procedure that takes an extended period of time the degree of permitted perfusion can be reduced or increased, or complete occlusion can be established, as required or desired as the procedure proceeds.

Optionally, the actuation mechanism includes a tension member. Placing the tension member in tension may cause the anchor section to assume a deployed or bent configuration.

In some embodiments of the invention, the anchor section includes at least one expandable member mounted to an outer surface of the catheter body to both occlude the CS and anchor the catheter at the same time. The at least one expandable member may include at least one balloon, at least one basket or umbrella-shaped structure, or at least one other expandable structure (e.g., at least one sleeve or a fluidly expandable film of material or the like).

Thus, disclosed herein is a catheter for anchoring an electrode in a stable position relative to a CS, including: an elongate catheter body adapted to be inserted into a portion of the CS or vein extending therefrom; at least one partial- or completely-occluding anchor ("anchor") structure coupled to the catheter body; and at least one electrode on the catheter body. The at least one anchor is movable between an undeployed configuration, wherein the catheter body is movable relative to the CS, and a deployed configuration, wherein the at least one anchor engages a tissue surface of the CS to inhibit movement between the catheter body and the CS at least partially, if not necessarily completely occluding the CS.

According to another aspect of the invention, a catheter for anchoring an electrode in or to a peripheral portion of the CS includes: an elongate catheter body having a central axis and a flexible anchor segment, the flexible anchor segment being movable between a deployed configuration, wherein the flexible anchor segment is deviated from the central axis of the catheter body to engage a tissue surface of the CS such that relative movement between the catheter body and the CS is inhibited without necessarily completely occluding the CS, and an undeployed configuration, wherein the flexible anchor segment is generally collinear with the central axis of the catheter body to introduce the catheter into the coronary sinus; and at least one marker band or electrode on the catheter body. Although complete or substantially complete occlusion is typically a more desirable condition, especially for mitral isthmus ablation procedures, as described more fully herein.

In some embodiments of the invention, the flexible anchor segment is biased into the undeployed configuration, and the catheter further includes a tension member. By placing the tension member in tension, the flexible anchor segment may be moved into the deployed configuration. In other embodiments of the invention, the flexible anchor segment is biased into the deployed configuration, and a sheath, stylet, guide wire, or other suitable straightening device may be used to move the flexible anchor segment into the undeployed configuration. Of course, the flexible anchor segment may be positioned as desired along the catheter body, including within an intermediate section of the catheter body or at the distal end of the catheter body and includes at least one (active) marker band or electrode to be selectable as a spatial references for generation of geometries or models and for visualization in conjunction with other active elements using an electroanatomical system.

The present invention also provides a method of generating a cardiac geometry, including the steps of: providing a CS catheter having an anchor structure and at least one marker band or electrode thereon; introducing the CS catheter into the CS or portion thereof; deploying the anchor structure to engage at least one tissue surface of the coronary sinus, thereby inhibiting relative movement between the CS catheter and the CS; and conducting a cardiac mapping operation using the electrode on the CS catheter as a reference electrode.

An advantage of the present invention is that it permits a reference electrode to be positively anchored within a vessel, thereby facilitating creation of anatomical geometries during or prior to performing a medical procedure (e.g., cardiac mapping and/or ablation). Another advantage of the present invention is that it positively anchors a reference electrode within a vessel while optionally preserving a degree of perfusion through the vessel, if desired to limit or minimize stasis and thrombus creation and enhancing dwell time for an extended period of time.

In a further aspect, a method is provided for creating a bi-directional mitral isthmus block in a heart. The method includes inserting an occlusion catheter into a CS of the heart, inserting an ablation catheter into a left atrium of the heart, expanding a balloon on the occlusion catheter, and ablating a portion of the myocardium to create a bi-directional isthmus block while the balloon is expanded.

DETAILED DESCRIPTION OF THE INVENTION

The invention set forth below in detail describes, depicts, and claims methods and systems to create ablation lines in the myocardium and optionally to generate anatomical geometry (and activation maps and the like) of at least a portion of said myocardium and also optionally, surrounding tissue. Prior to initiation of the ablation, an occlusion catheter is positioned within a vessel, such as the coronary sinus (CS), to completely or substantially prevent blood flow therethrough during the ablation procedure (i.e., reduce or temporarily halt perfusion). Endocardial ablation is then initiated while the CS is occluded (e.g., from the left atrium adjacent the CS). It has been found that ablation lines, or lesions, extending completely through the myocardium (i.e., transmural lesions) that are created near the CS after it has been occluded are formed more easily than if the CS were not occluded. In the example set forth below, it is shown that such occlusion of the CS during the creation of a mitral isthmus ablation line(s) readily occurs (oftentimes with less power, or energy delivered to target tissue, than would be used without occlusion of the CS and/or the time for creation of the ablation line(s) is shorter).

The systems and methods set forth herein are not limited to the specific embodiments described herein. In addition, components of each system and steps of each method can be practiced independently and separately from other components and method steps described herein. Each component and method step also can be used in combination with other catheters, balloons, systems, and methods, for example.

Figure 1:
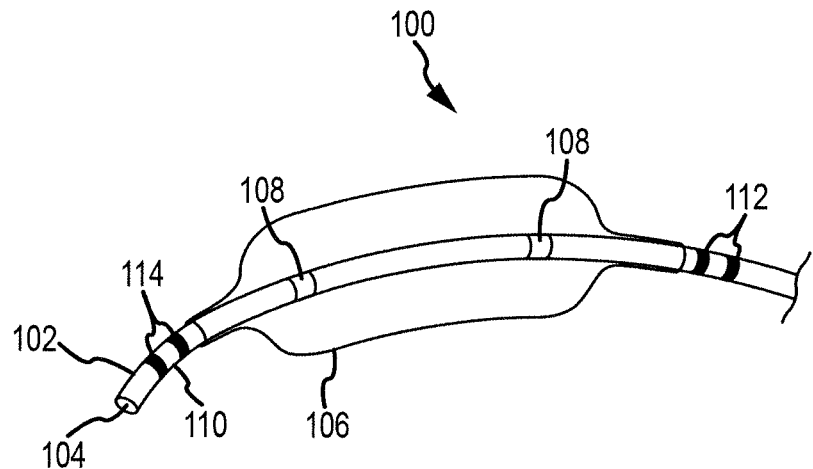
FIG. 1 is a schematic view of a CS occlusion system in accordance with one embodiment of the invention.

FIG. 1 illustrates a CS occlusion system 100 in accordance with one embodiment of the invention. System 100 includes a catheter 102 having a distal end 104 and a proximal end (not shown). In one embodiment, the proximal end of the catheter shaft comprises a braided catheter shaft constructed for example with 304 stainless steel braid incorporated into a nylon 11 polymer. An exemplary dimension for the braid is about 0.002" by about 0.006" (individual filars). Of course, other suitable types, or grades, of stainless steel can be utilized when practicing the teaching herein, including a braid having one or more substantially flat cross-sectional dimensions (e.g., a "flat braid"). In one form of the invention the braid, or flat braided portions, are disposed at least adjacent the proximal portion of the balloon. That is, the catheter 102 may also be a braided catheter wherein the catheter wall includes a cylindrical and/or flat braid of metal fibers, for example, stainless steel fibers (see FIGS. 11 and 12 for general location of such flat braid denoted by reference numeral 63). Such a metallic braid may be included in the catheter 102 to add stability to the catheter 102 and also to resist radial forces that might crush the catheter 102. Metallic braid also provides a framework to translate force imparted by the clinician on the proximal end of the catheter 102 to the distal end 104 to urge an occlusion structure, such as a balloon 106, disposed on the catheter 102 into a desired, or appropriate, location, for example. The flat wire, or other types of wire, braid can be thought of as a so-called backbone for the catheter. In this regard nonprovisional U.S. patent application Ser. No. 11/723,729 filed 21 Mar. 2007 assigned to St. Jude Medical, Atrial Fibrillation Division, Inc. (now U.S. Pat. No. 7,706,891) is hereby incorporated herein in its entirety. Other materials can be used to fabricate the backbone portion provided that they have appropriate mechanical characteristics. One reason for including the braided catheter shaft is that stiffer shaft material is desirable, if not simply necessary, to help the catheter maintain its position within the CS when the balloon is inflated and thus continue to occlude the CS. This characteristic of a catheter is sometimes referred to as having adequate "pushability" in certain contexts. Catheter 102 has a tubular body with a passageway extending therethrough. A balloon 106 is located near distal end 104. In one embodiment, balloon 106 is a polyurethane balloon located 1.5 cm from distal end 104, or at a convenient and appropriate distance from the distal end 104. It should be recognized that balloon 106 could be manufactured from other materials and could be located closer or further from distal end 104 than 1.5 cm. In another embodiment, balloon 106 is manufactured from an elastomeric material such as silicone. As shown in FIG. 1, balloon 106 has a substantially cylindrical shape, although other shapes can be utilized to increase the likelihood that occlusion of the CS will result for a specific anatomical topography of a given patient or subject (as further described and depicted herein, and specifically including substantially cylindrical as well as gradually tapered shapes and the like).

Catheter 102 also includes a plurality of spaced apart marker bands 108 located under balloon 106. In one embodiment, catheter 102 includes one, two, or more electrodes or marker bands 108 manufactured from a radio-opaque material, as known in the art, to allow for physiologic sensing, therapy delivery, and/or fluoroscopic visualization of catheter 102. In another embodiment, marker bands 108 are located on catheter 102 at locations other than under balloon 106. The marker bands can include traditional radio-opaque material as noted above, such as platinum, gold, steel, or the like and can also, in lieu of or in addition to, these materials include miniature magnetic coils for locating or visualizing the catheter in vivo (e.g., displaying location, orientation, motion, etc.) using for example one of a variety of electroanatomical systems. For example, the EnSite™ impedance-based system or the MediGuide technology magnetic-based system which are both owned by St. Jude Medical, Inc. of St. Paul, Minn. can be used in conjunction with the occlusion catheter of the invention along with various ablation catheters for treating AF. With regard to the MediGuide technology, U.S. Pat. No. 6,233,476 to Strommer et al. issued 15 May 2001 describes a magnetic-based Medical Positioning System that can be utilized according to this disclosure and the contents of which are hereby incorporated by reference as if fully set forth herein. Also, the Aurora system from Northern Digital of Waterloo, Ontario, Canada or the Carto System from Biosense Webster of Diamond Bar, Calif. The systems interact with one or more active electrodes coupled to a portion of one or more catheters (shaft portion, proximal or distal of the balloon, etc.) and used in reference to reference electrodes so that the location, orientation, or motion of the catheter can be derived. In the case of the EnSite™ impedance-based localization and visualization system from. St. Jude Medical, Inc. one or more impedance-based reference electrodes disposed in a stable position provide spatial reference for other, roving catheters having one or more electrodes. In related embodiments, the marker bands 108 and one or more of the electrode pairs 112,114 can likewise be adapted for visualization or localization according to the various modalities of the foregoing systems. Of course, while not specifically depicted herein additional structures can be coupled to the catheter 102 for the purpose of visualization and localization of the catheter 102 during a procedure on a subject. In addition, the balloon itself can include at least one reference electrode or magnetic coil for the electroanatomical system such that an occlusion catheter having the balloon (in combination with an optional relatively stiffened distal portion) on the catheter shaft retains the electrode in place thereby increasing positional accuracy to the system.

In addition, the balloon 106, 130, 150, 160, 180 can be fabricated from a mixture of biocompatible resin-based material infused or combined with a radio-opaque material or can have segments of radio-opaque material printed or applied to an interior or exterior surface thereof.

Catheter 102 can include a bend 110 located between balloon 106 and distal end 104. Bend 110 facilitates cannulization of the CS by allowing easier access to the CS opening and can promote fixation within a portion of the great cardiac vein distal to the os of the CS. In one embodiment, bend 110 comprises a single bend of between 25 and 75 degrees, and more particularly between 30 and 60 degrees, and more particularly still, is about 45 degrees. Bend can also comprise a compound bend or serpentine configuration. In one embodiment, bend 110 is located within about four (4) centimeters of distal end 104, and more particularly is located within about two (2) centimeters of distal end 104, and more particularly still, is located about one and one-half (1.5) centimeters from distal end 104. In addition, catheter 102 can be curved proximally of bend 110. This curvature further facilitates cannulization of the CS as well as proper placement of balloon 106 within the CS. In certain forms of the foregoing the distal end 104 is fabricated to include a so-called atraumatic tip portion. In one embodiment the tip portion is constructed from a relatively lower durometer material in relation at least the adjacent portions of the main shaft, or body, of the catheter 102. For example the tip portion can be fabricated from 35D polyether block amide (or PEBA) that is, a thermoplastic elastomer (TPE), commonly referred to under the trademark Pebax in its unmanufactured form. In this example, the shaft of the catheter 102 might have a durometer of 45 D-55 D or higher, for example.

Catheter 102 also can include a pair of electrodes 112,114. A first electrode pair 112 is located on catheter 102 proximally of balloon 106 and a second electrode pair 114 is located on catheter 102 distally of balloon 106. Electrode pairs 112,114 are utilized to detect the presence and absence of errant electrical signals in the myocardium (wall of the heart). Each electrode 112,114 is connected to an elongate conductor or lead (not shown) that extends within a lumen or a wall portion of the catheter 102. In one embodiment, each electrode of the pair of electrodes 112,114 comprises a ring-type electrode. By electrically coupling two of the four depicted electrodes 112,114 to an electrode separated from each other by the balloon or expandable member 106 the desired bi-directional conduction block resulting from an effective lesion set can be confirmed in substantially real-time during an ablation procedure. Alternatively or in addition, one of the distal pair of electrodes 114 can be electrically coupled to a remote electrode (not shown) such as a surface electrode adhered to the skin of a subject or within the vicinity of the catheter 102 to confirm conduction block from within the target vessel.

Figure 2:
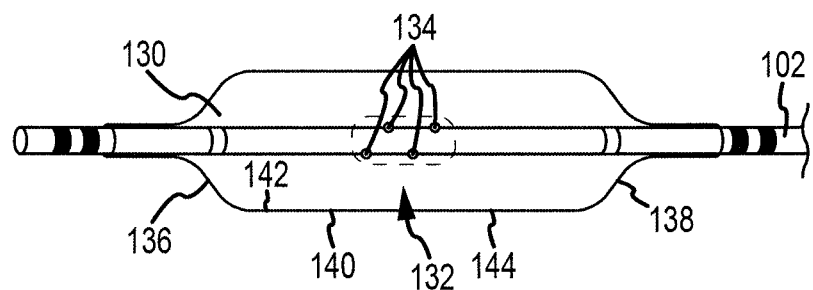
FIG. 2 is a schematic view of an alternative balloon to be used with the catheter shown in FIG. 1.

FIG. 2 illustrates an alternative balloon 130 suitable for use with catheter 102. Balloon 130 is similar to balloon 106 except that balloon 130 includes a temperature sensing array 132 having multiple sensors 134 positioned such that accurate temperature readings can be obtained of adjacent tissue. Sensors 134 are positioned at a first end 136 and/or a second end 138 of balloon 130, at a middle 140 of balloon 130, or at any location along balloon 130. In one embodiment, sensors 134 are miniature T-type thermocouples, thermistors, or any other type of sensor that can be utilized to sense temperature of adjacent tissue. In exemplary embodiments, sensors 134 are disposed against an interior surface 142 of balloon 130, an exterior surface 144 of balloon 130 and/or within balloon 130 and spaced apart from interior surface 142 of balloon 130.

As shown in FIG. 1, catheter 102 is curved and, accordingly, includes an inner curvature. Array 132 is located at the inner curvature to facilitate positioning of thermocouple array 132 in the area of the mitral isthmus ablation line. In one embodiment, a marker is positioned proximate array 132 to facilitate accurate orientation of balloon 130 with regard to the atrial portion of the CS. As shown in FIG. 2, four sensors 134 are arranged in an array that is about two (2) mm wide by about six (6) mm long, with two (2) mm spacing between sensors. Leads (not shown) extend from each sensor 134 along catheter 102 to a multiple channel data logger (not shown) connected to a standard computer (not shown) via an RS 232 serial link (not shown).

Figure 3:
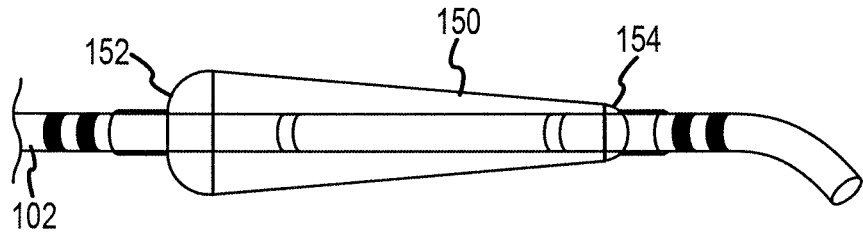
FIG. 3 is a schematic view of a further alternative balloon to be used with the catheter shown in FIG. 1.

FIG. 3 illustrates a further alternative balloon 150 suitable for use with catheter 102. Balloon 150 has a rounded frusto-conical shape that tapers from a proximal end 152 to a distal end 154. In one embodiment, the taper is about a seven (7) degree included angle.

Catheter 102 includes an inflation port (not shown) that is used to supply fluid to balloons 106, 130, 150 (etc.). In one embodiment, the inflation fluid is a gas such as air or $CO_2$. In another embodiment, the inflation fluid is a liquid such as saline or water. In yet another embodiment, the fluid can comprise a radio-opaque fluid or so-called contrast media to promote visualization of the location and shape of the balloon via fluoroscopy. Along the same lines a relatively inert fluid could also include minute metallic particles or fibers to promote visualization or localization. In addition or in lieu of the foregoing a portion of interior or exterior of the balloon can be coated with a metallic film or the like (including magnetic film) to further enhance visualization or localization of the balloon 106, 130, 150 (etc.) and hence, the catheter 102 during a procedure utilizing one or more of the visualization and localization systems noted hereinabove. In a related embodiment, a biocompatible resin-based film of material for fabricating the balloon can be infused with particles (e.g., so-called nanoparticles, nanotubes, and the like) during the manufacturing process thereby rendering the balloon visible via a number of imaging modalities.

Figure 4:
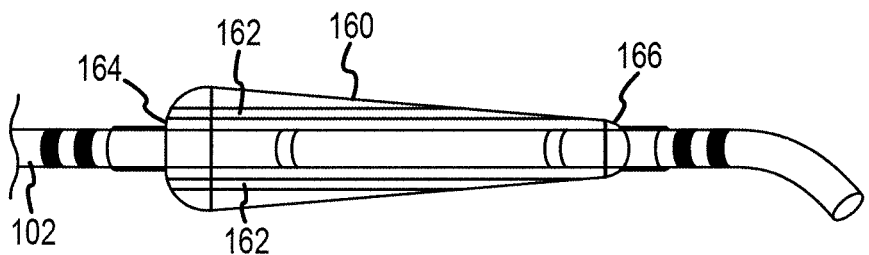
FIG. 4 is a schematic view of a further alternative balloon to be used with the catheter shown in FIG. 1.

FIG. 4 illustrates an alternative balloon 160 positioned on catheter 102. Balloon 160 includes a plurality of passageways 162 extending from a proximal end 164 of balloon 160 to a distal end 166 of balloon 160. Passageways 162 permit blood to flow therethrough while balloon 160 is inflated and contacting an interior surface of the vessel into which catheter 102 has been positioned. Passageways 162 are configured such that blood flow will be spaced from the vessel wall thus permitting a fluid gap to be located between the flowing blood and the vessel wall. The fluid filling balloon 160 is, in one embodiment, a gas such as one of air and $CO_2$. Alternatively, the fluid is a liquid such as water, saline, or Heparinized saline or the like.

Figure 5:
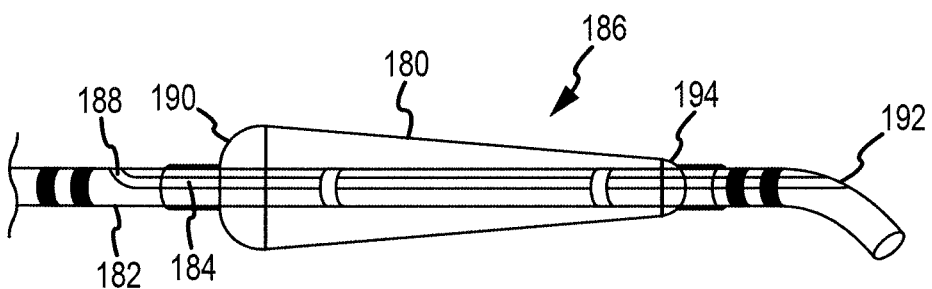
FIG. 5 is a schematic view of a further alternative balloon to be used with an alternative catheter.

FIG. 5 illustrates a further alternative balloon 180 positioned on catheter 182. A passageway 184 extends through a distal portion 186 of catheter 182. Passageway 184 includes a first opening 188 at a position proximal of a proximal end 190 of balloon 180 and a second opening 192 at a position distal of a distal end 194 of balloon 180. In operation, blood is permitted to flow through passageway 184 when balloon 180 is expanded and contacting an interior surface of the vessel into which catheter 182 has been positioned.

The method of using the above described CS occlusion system (shown in FIGS. 1-3) will next be described.

A sheath containing the occlusion catheter is inserted into one of the femoral artery and the internal jugular. In one embodiment, the sheath is an 8Fr, Fast Cath™ model, available from St. Jude Medical, Inc. of St. Paul, Minn. The sheath is manipulated through the vascular system so that it enters a chamber of the heart, such as the left atrium. The occlusion catheter is extended distally from the sheath until the balloon on the catheter is distal of the distal end of the introducer sheath. The catheter is manipulated to allow a distal tip of the catheter to enter the vessel to be occluded. The extended catheter is inserted into the vessel such that the balloon is at least partially within the vessel. In one embodiment, the vessel is the CS and the balloon is completely contained within the vessel and located adjacent to, and/or overlying, a portion of the myocardium to be ablated. In the embodiment illustrated in FIGS. 1-3, a pair of marker bands is included on the catheter. These marker bands promote accurate placement of the catheter within the vessel to be occluded and can be used to aid electroanatomical visualization and localization as described elsewhere herein.

An ablation catheter is then manipulated through the vascular system so that the ablation catheter enters a chamber of the heart, such as the left atrium. In one embodiment, the ablation catheter also includes diagnostic capability used to map relevant geometries and/or electrical activity within the chamber. When the ablation catheter is located within the left atrium, such geometries include one or more of the left atrial appendage, the right superior pulmonary vein, the inferior pulmonary trunk, and the left atrial body. In an alternative embodiment, the above described mapping is performed using a separate mapping system coupled to a mapping and/or therapy delivery catheter. As noted herein an exemplary mapping system includes the EnSite system with NavX surface patches (or the EnSite Velocity version of the EnSite system), available from St. Jude Medical, Inc.

The ablation catheter is then utilized to ablate portions of the myocardium. The ablation energy and delivery technology includes, by way of example and without limitation one or more of the following: cryogenic, RF, laser, microwave, ultrasound (including high intensity focused ultrasound, or HIFU) and microwave. In one embodiment, ablation lesions are created on the atrial myocardium overlying the CS. The ablation lesions extend through the myocardium and prevent errant electrical signals from passing across the portion of the myocardium that has been ablated. In an exemplary embodiment, an ablation lesion is created that extends from proximate the left inferior pulmonary vein to proximate the mitral valve. Such an ablation lesion is sometimes referred to as a mitral isthmus line. It is this region of the myocardium that overlies the CS. Accordingly, when the CS is occluded, blood does not flow adjacent this portion of the myocardium and it has been found that a lower power setting can be used on the ablation catheter and/or the ablation is completed within a shorter time, than when blood is flowing through the CS.

According to an aspect of the invention a gas filled balloon is located within the portion of the CS that is adjacent to, and/or overlies this portion of the myocardium, and thus heat is not removed from the myocardium as efficiently as when blood is flowing through the CS. The absence of significant reduction of blood flow thus allows more efficient and relatively rapid ablation of this portion of the myocardium. In one embodiment, due at least in part to this increased efficiency, ablating within the CS is not used when the above described CS occlusion catheter is used. In another embodiment, due at least in part to the increased efficiency, the number of ablation lesions created when the above described CS occlusion catheter is used is less than when the CS occlusion catheter is not used.

As described above, located on the occlusion catheter is a pair of electrodes. These electrodes are utilized to determine whether errant electrical signals are passing through the portion of the myocardium being monitored. In one embodiment, the occlusion catheter is used to monitor these signals before, during, and/or after the ablation procedure, and to gather information so that a determination can be made as to whether the ablation procedure has stopped the errant electrical signals.

Figure 6:
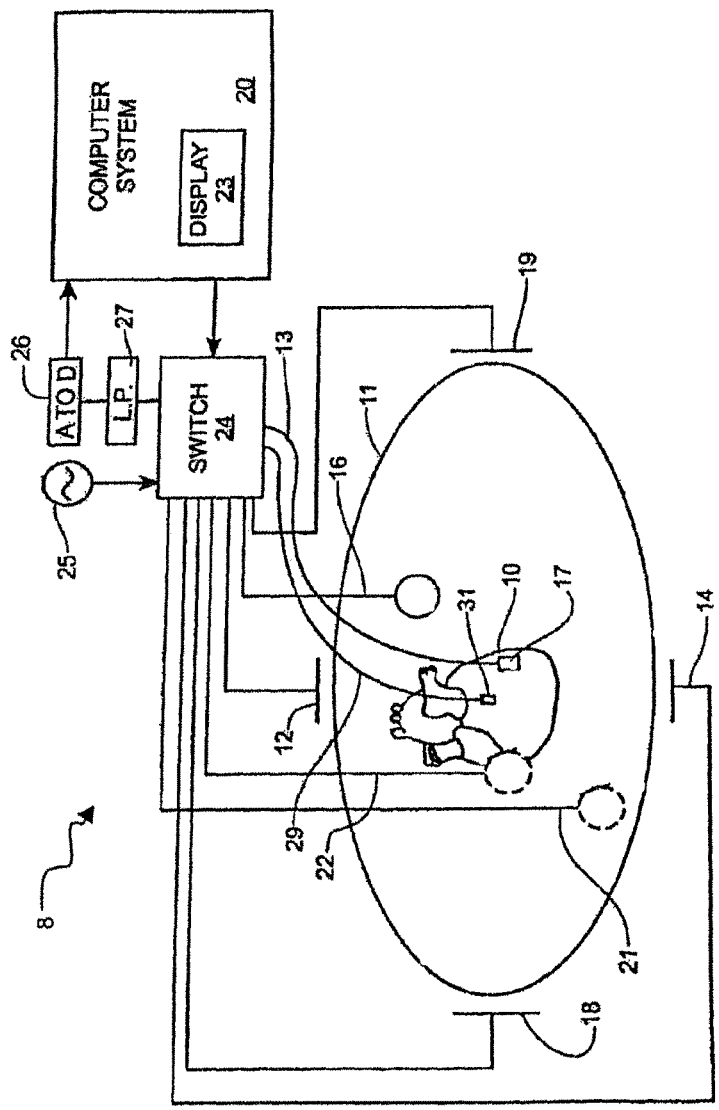
FIG. 6 is a schematic diagram of a localization system utilized in an electrophysiology study.

FIG. 6 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. Three sets of surface electrodes (e.g., patch electrodes) are shown applied to a surface of the patient 11, defining three generally orthogonal axes, referred to herein as an x-axis, a y-axis, and a z-axis. The x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18,19 are applied to the patient along a second axis generally orthogonal to the x-axis, such as along the inner thigh and neck regions of the patient, and may be referred to as the Left Leg and Neck electrodes. The z-axis electrodes 16,22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra cardiac electrode 31, described in further detail below. It should also be appreciated that, in addition, the patient 11 may have most or all of the conventional electrocardiogram (ECG) system leads in place. This ECG information is available to the system 8, although not illustrated in FIG. 6.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

An optional fixed reference electrode 31 (e.g., attached to a wall of the heart 10) is shown on a second catheter 29. For calibration purposes, this electrode 31 may be stationary (e.g., attached to or near the wall of the heart and/or in the CS) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein. The computer 20 may also comprise a display 23. An analog-to-digital converter 26 and low-pass filter 27 may be operatively connected to computer 20 and switch 24.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. Preferably, the coordinate system is a three-dimensional (x, y, z) Cartesian coordinate system, though the use of other coordinate systems, such as polar, spherical, and cylindrical coordinate systems, is within the scope of the invention.

As should be clear from the foregoing discussion, the data used to determine the location of the electrode(s) within the heart is measured while the surface electrode pairs impress an electric field on the heart. The electrode data may also be used to create a cardiac geometry including a respiration compensation value used to improve the raw location data for the electrode locations as described in U.S. Pat. No. 7,263,397 to Hauck et al. issued 28 Aug. 2007 hereby incorporated herein in its entirety. The electrode data may also be used to compensate for changes in the impedance of the body of the patient as described in co-pending U.S. patent application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc., which generates the electrical fields described above. Other localization systems, however, may be used in connection with the present invention, including for example, the Carto navigation and location system of Biosense Webster, Inc., the MediGuide technology owned by St. Jude Medical, Inc., or the Aurora system of Northern Digital Inc., both of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether an electrical field (e.g., EnSite NavX™), a magnetic field (e.g., Carto, MediGuide technology, Aurora), or another suitable field, may be referred to generically as "localization fields," while the elements generating the fields, such as surface electrodes 12, 14, 16, 18, 19, 22 may be generically referred to as "localization field generators." As described above, surface electrodes 12, 14, 16, 18, 19, 22 may also function as detectors to measure the characteristics of the localization field (e.g., the voltages measured at roving electrodes 17, 52, 54, 56). Though the present invention will be described primarily in the context of a localization system that generates an electrical field, one of ordinary skill in the art will understand how to apply the principles disclosed herein in other types of localization fields (e.g., by replacing electrodes 17, 52, 54, 56 with coils to detect different components of a magnetic field).

As described above, localization system 8 may employ one or more reference electrodes 31, carried on one or more catheters 29, as a reference for the three-dimensional coordinate system of localization system 8. Accordingly, it is desirable for reference electrodes 31 to be positively retained (often referred to as "anchored") at the desired location for the reference of the three-dimensional coordinate system, often within the CS.

Figure 7:
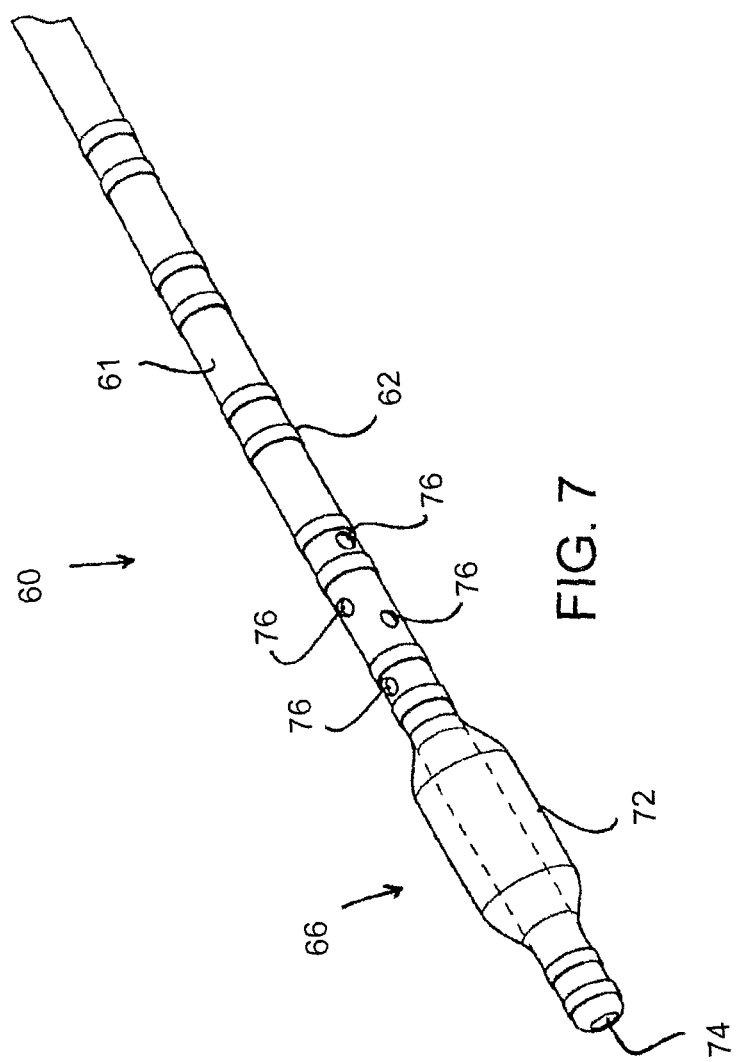
FIG. 7 illustrates another embodiment of a catheter to anchor an electrode in a vessel, such as the CS, including a balloon to provide bias against the vessel wall.

FIG. 7 illustrates another embodiment of a catheter to anchor an electrode in a vessel, such as the CS, including a balloon to provide bias against the vessel wall. FIG. 7 illustrates a second embodiment of a catheter 60 having an anchor section 66 for anchoring one or more electrodes 62 within a CS. In the embodiment illustrated in FIG. 7, anchor section 66 includes at least one balloon 72 positioned about a circumference of catheter body 61. Balloon 72 is fluidly coupled to an inflation fluid source (not shown), in order to inflate balloon 72 from the undeployed configuration (not illustrated) into the deployed configuration (illustrated in FIG. 7), for example through inflation port 73 (shown in FIG. 11). Perfusion pathways may be provided by one or more perfusion passages through the interior of catheter 60, each of which includes a first opening 74 positioned distally of anchor section 66 (e.g., distally of balloon 72) and a second opening 76 positioned proximally of anchor section 66 (e.g., proximally of balloon 72). Alternatively, perfusion pathways may be provided by altering the shape of balloon 72 such that it does not completely occlude the CS, thereby permitting perfusion around the exterior of catheter 60.

Figure 8:
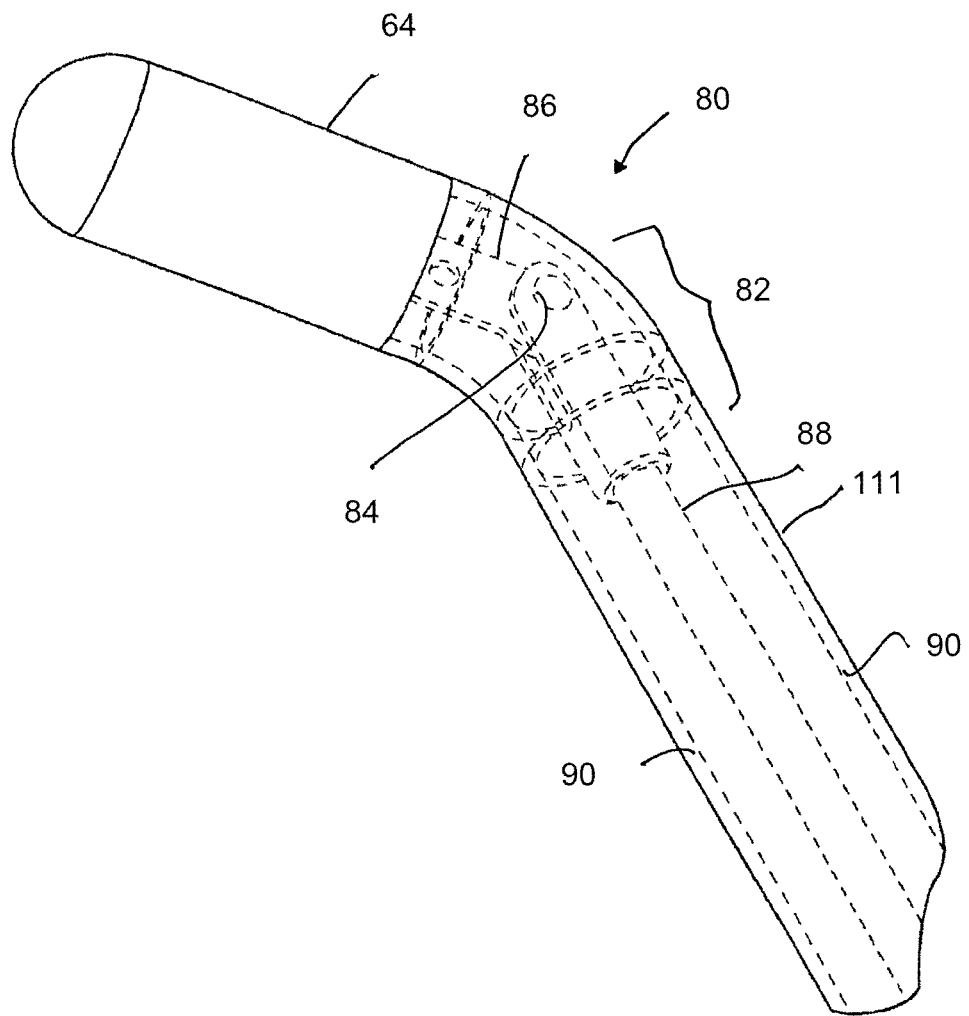
FIGS. 8-10 depict several actuation mechanisms to actuate a flexible anchor section of a catheter according to some aspects of the present invention.
Figure 9:
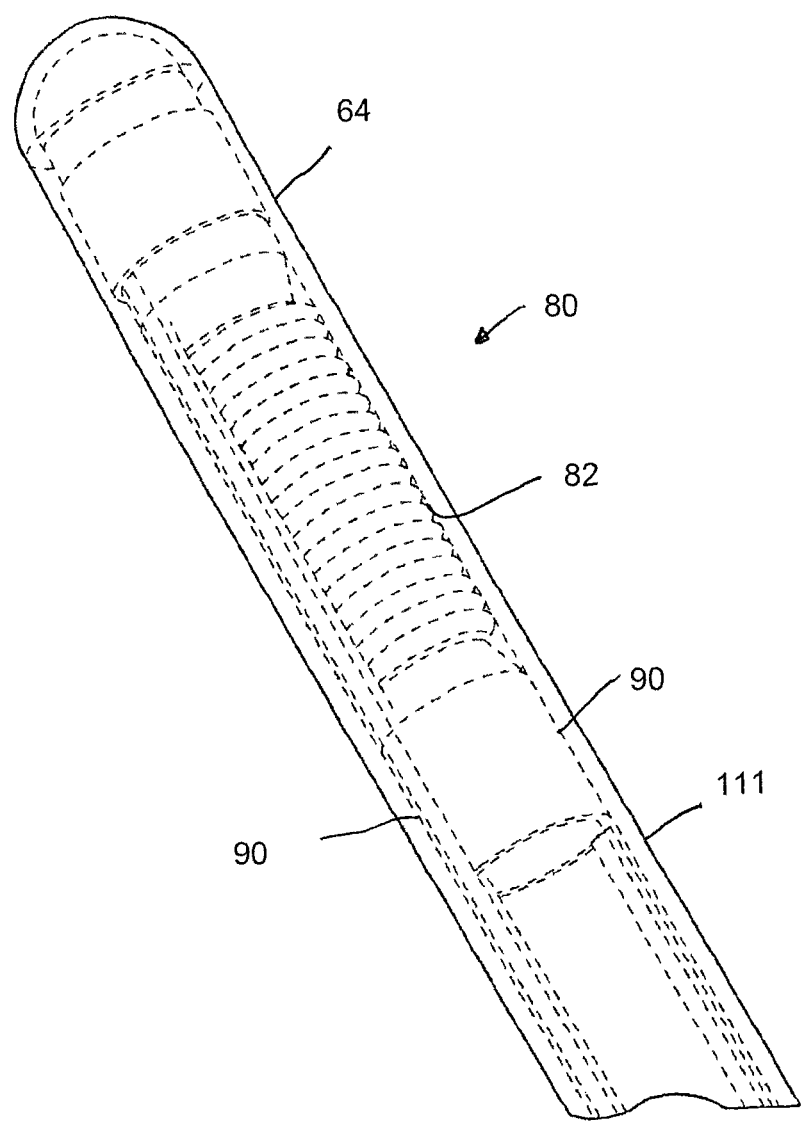
Figure 10:
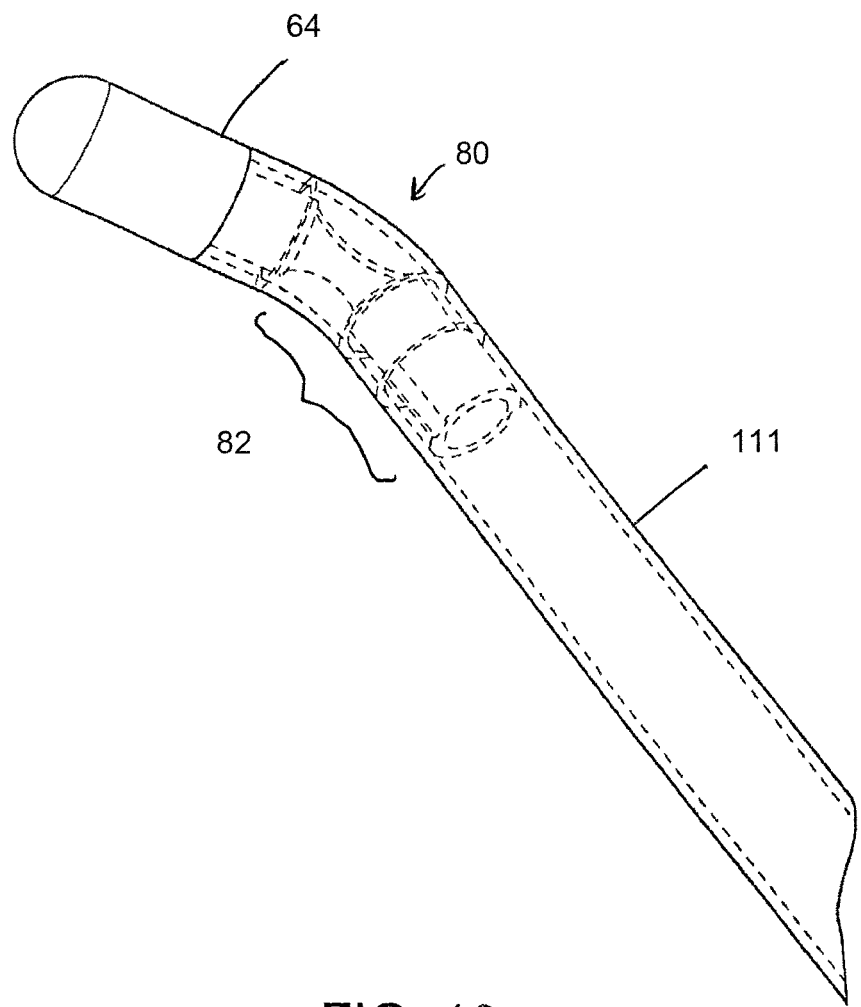

FIGS. 8-10 depict several actuation mechanisms to actuate a flexible section 80 of a catheter body 111 according to some aspects of the present invention. FIGS. 8-10 illustrate various actuating mechanisms (denoted generally by an arrow from reference numeral 80) for a flexible anchor segment positioned at the distal end 64 of catheter body 111. In FIG. 8, the actuating mechanism or assembly 82 includes a joint having a pin 84 joining two members 86,88 such that when a tension member 90 (e.g., two elongate wires or filaments as shown in FIG. 8) the distal end 64 deflects. In FIG. 9 the actuating mechanism or assembly includes a pleated or corrugated section (also denoted by reference numeral 82) which is also activated by wires or filaments 90 to deflect the distal end 64 relative to the catheter body 111. In FIG. 10, the actuating mechanism or assembly includes a hinge assembly (denoted by reference numeral 82) activated by wires or filaments 90 so that the distal end 64 pivots relative to catheter body 111.

The devices and methods disclosed herein may be practiced to good advantage in generating a cardiac geometry. A CS catheter having an anchor structure and an electrode may be provided and introduced into the CS. Once the catheter is positioned as desired, the anchor structure may be deployed to engage a tissue surface of the CS, thereby inhibiting relative movement between the CS catheter (and therefore any electrodes thereon) and the CS. The anchor structure may be any of the structures disclosed herein (e.g., sections of the catheter body having an expandable axial cross-section, wire anchors, anchor segments of the catheter body, and the like). With the electrodes so anchored, they may be used as reference electrodes for a cardiac mapping operation. As noted, the catheter may also be configured to preserve perfusion via a pathway through the CS from a distal side of the anchor structure or balloon to the other. As described above, the at least one perfusion pathway may be around the exterior of the catheter body and/or through the interior of the catheter body to thereby bypass the balloon and provide a modicum of perfusion.

Occasionally, it may be desirable to provide a catheter 131 that completely occludes the CS. This may be desirable, for example, where catheter 131 is to be employed in conjunction with an ablation procedure. In such contexts, blood flow through the CS may act as a heat sink, pulling heat away from an ablation site and preventing lesion creation. By occluding the CS, this heat sink effect may be mitigated.

Figure 11:
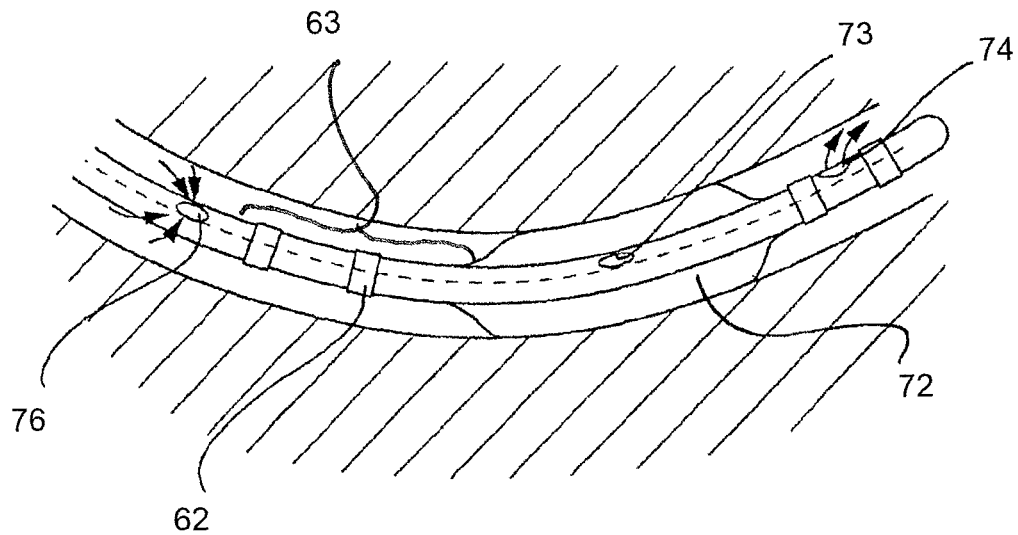
FIG. 11 depicts the catheter of FIG. 7 deployed within a vessel and illustrates perfusion across the balloon.

FIG. 11 depicts the catheter of FIG. 7 deployed within a vessel and illustrates limited, or highly reduced, perfusion "across" the balloon. This prevents catheter 60 from completely occluding the CS, even with anchor segment 66 in the deployed configuration, thereby minimizing stasis and thrombus creation and advantageously increasing dwell time of catheter 60 within the CS during a cardiac mapping operation.

FIG. 7 illustrates a second embodiment of a catheter 60 having an anchor section 66 for anchoring one or more electrodes 62 within a CS. In the embodiment illustrated in FIG. 7, anchor section 66 includes at least one balloon 72 positioned about a circumference of catheter body 64. Balloon 72 is fluidly coupled to an inflation fluid source (not shown), in order to inflate balloon 72 from the undeployed configuration (not illustrated) into the deployed configuration, for example through inflation port 73 (shown in FIG. 11). Perfusion pathways may be provided by one or more perfusion passages through the interior of catheter 60, each of which includes a first opening 74 positioned distally of anchor section 66 (e.g., distally of balloon 72) and a second opening 76 positioned proximally of anchor section 66 (e.g., proximally of balloon 72). Alternatively, perfusion pathways may be provided by altering the shape of balloon 72 such that it does not completely occlude the CS, thereby permitting perfusion around the exterior of catheter 60. Also depicted in FIG. 11 (and FIG. 12) is a region proximal of the balloon 72 that includes structural reinforcement (denoted generally by reference numeral 63) to enhance the so-called pushability of the distal end and, in particular the balloon 72 during CS occlusion. The structural reinforcement 63 can include an embedded braided segment of the shaft of the catheter including one or more flat wire filars (e.g., wire having a lateral dimension greater than an axial dimension). The structural reinforcement 63 can extend partially or wholly toward the proximal end of the catheter but in the case that the catheter is deployed within a delivery sheath or introducer, the structural reinforcement 63 does not necessarily need to extend all the way to the proximal end of the catheter.

Figure 12:
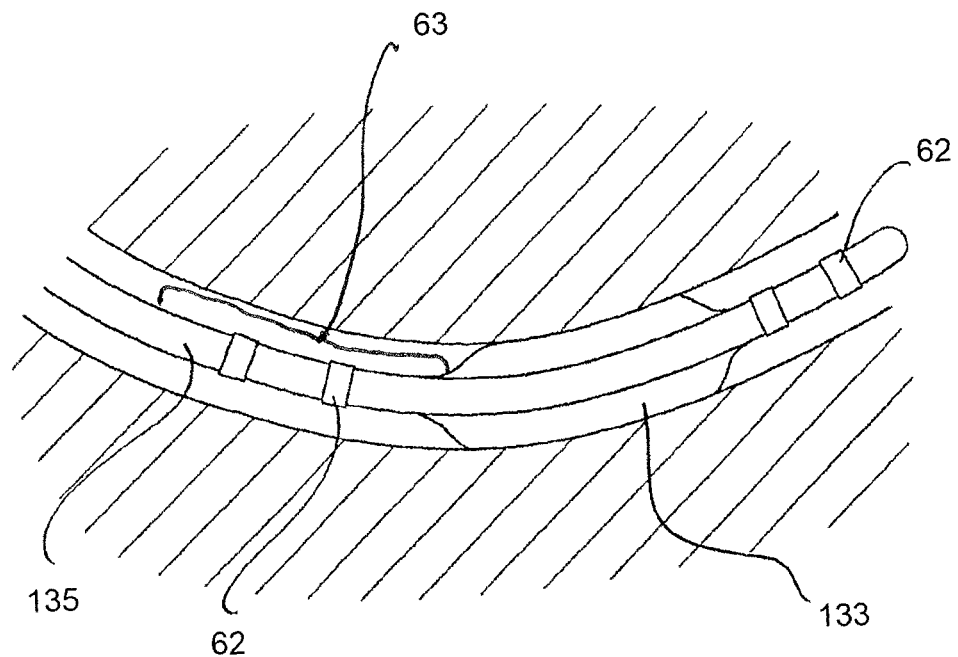
FIGS. 12-14 illustrate a balloon catheter that may be anchored within a vessel, such as the coronary sinus, to substantially completely occlude the vessel.
Figure 13:
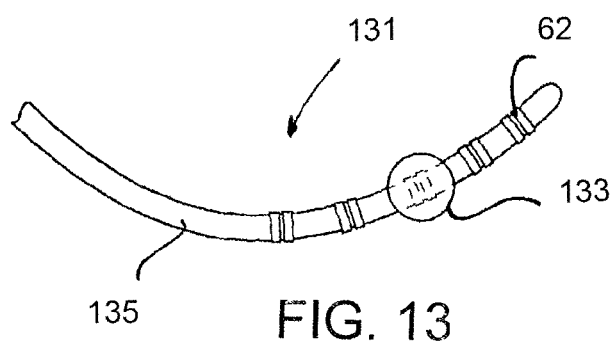
Figure 14:
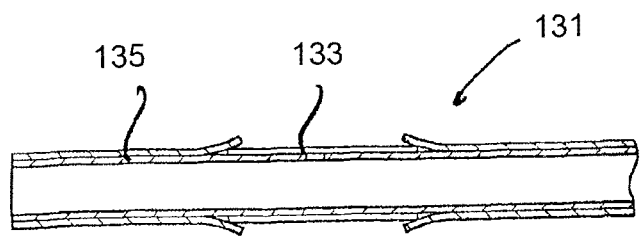

FIGS. 12-14 illustrate a balloon catheter that may be anchored within a vessel, such as the CS, to substantially completely occlude the vessel. Accordingly, as shown in FIGS. 12-14, catheter 131 may include an elongate catheter body 135 and a balloon 133, as well as one or more electrodes (e.g., electrodes 62). When balloon 133 is deflated (FIG. 14), catheter 131 may be introduced into and/or removed from the CS. When balloon 133 is inflated (FIG. 12), it occludes the CS. Of course, balloon 133 also serves to anchor catheter 131 relative to the CS.

Although several embodiments of this invention have been described above with a certain degree of particularity, those skilled in the art could make numerous alterations to the disclosed embodiments without departing from the spirit or scope of this invention. For example, though the reference electrode has been described herein as anchored in the CS, the principles disclosed herein could be employed to anchor the reference electrode in any blood vessel.

Similarly, though the electrode has been described herein as a reference electrode for a localization system, the devices and methods described could also be practiced to position a therapeutic element, such as an RF ablation electrode or other ablation element.

In a further embodiment, the occlusion system includes an introducer sheath utilized to position the occlusion catheter at the CS. In this embodiment, the catheter extends through the introducer sheath and, upon arrival at the CS, is extended distally beyond a distal end of the introducer sheath. In one embodiment, the sheath is a steerable sheath that can be manipulated through the use of wires or other means to bend or curve as it passes through the vascular system, thus bending or curving the catheter therewithin. As noted with respect to the catheter, either or both of the catheter and the sheath can include reinforced portion(s) at least near the balloon to enhance the pushability of each to provide stability to the balloon during CS occlusion. Such reinforced portions can include, for example, braided portions having one or more filars of flat wire braid, or the like.

Example A

Experiments were conducted on nine female pigs using the above identified occlusion system. Vascular access was obtained via standard angiography sheaths in the right femoral artery (8Fr, Fast Cath™ model, available from St. Jude Medical, Inc. of Little Canada, Minn.) and the right internal jugular (10Fr).

Transseptal access was obtained under fluoroscopic guidance with a Daig SL-1 sheath (available from St. Jude Medical, Inc.). A quadripolar electrode, placed in the right coronary cusp, was used as a reference for the electroanatomical mapping system (EnSite NavX, St. Jude Medical, Inc.). Separate geometries and associated electrical activity of the left atrial appendage, the right superior pulmonary vein, the inferior pulmonary trunk, and the left atrial body were acquired using a circular mapping catheter.

Ablation was performed using a 3.5 mm Celsius Thermo-Cool (available from Biosense Webster, Inc. of Diamond Bar, Calif.). A maximum of 35 watts power was used in the last seven (7) swine and 50 watts were used in the first 2 animals. All RF ablations were performed for one (1) minute with an irrigation rate of about 30 cc/min.

For each swine, two linear ablations lines (proximal and distal) were created over the atrial myocardium overlying the CS. The proximal line was placed more between the inferior border of the inferior pulmonary vein trunk and the mitral annulus. The distal line was located between the inferior border of the left atrial appendage and the mitral annulus. In each swine, the CS was completely occluded with the CS occlusion balloon during RF ablation for one of the lines. The CS occlusion balloon was positioned with the center of the balloon under the ablation line. The CS balloon was then inflated with approximately five (5) mls of air and occlusion of the CS and the great cardiac vein was confirmed by contrast injection through the catheter internal lumen. The position of the line that was created during CS occlusion was alternated between swine. The CS balloon was removed during RF application for the ablation line without occlusion to prevent blood flow limitation. Biophysical parameters of each RF application were continuously recorded in the electrophysiology recording system.

The CS occlusion catheter utilized is illustrated in FIG. 2.

At the end of the procedure, 2,3,5-triphenyl-2H-tetrazolium chloride was administered intravenously and the animals were euthanized with an intravenous injection of Euthasol 20 ml (390 mg pentobarbital sodium and 50 mg phenyloin sodium per ml, Delmarva Laboratory, Midlothian, Va.). A lateral thoracotomy was then performed with an incision through the left 4th intercostal space. The heart was examined in situ for the presence of pericardial bleeding. The endocardial surface of the excised heart was then examined by creating an incision in the left atrium to allow inspection and photography of the left atrial aspect of the mitral isthmus.

The CS was opened posteriorly through its free wall for inspection of possible dissection and to assess transmurality of each line. Ablation lines were also examined and photographed longitudinally with a macro camera (Nikon D50, Micro Nikkor 60 mm f2.8, Nikon Corporation, Melville, N.Y., USA) to assess transmurality and for off-line measurements. Ablation lesion characteristics were measured using custom software written with the Matlab programming language (Mathworks).

A total of 18 endocardial ablation lines were placed over the CS for the nine swine used in the study (i.e. a proximal and distal line for each swine). In one swine, the occlusion balloon could not be properly positioned and therefore two lines were placed without CS occlusion. Therefore, eight (8) ablation lines were placed during CS balloon occlusion and 10 lines were placed without CS occlusion. All lines were identified at necropsy. However, at post mortem examination, one of the proximal ablation lines was found to be located within the left atrial appendage superior to the CS and therefore, this line was not included in the data analysis.

The left atrial wall thickness was 2.9±1.3 mm for the endocardial lines without CS occlusion and 3.4±1.1 mm for the endocardial lines with CS occlusion (p=0.5). Similarly, the mean number of RF applications was 6.2±1.5 and 6.3±1.2 respectively during CS occlusion and when the CS balloon was not inflated. Catheter temperature and mean power were not significantly different when CS occlusion was compared to no-occlusion. Moreover, impedance drop was not different between these two conditions.

All linear lesions deployed during CS occlusion were transmural. Conversely, only one (1) out of 10 lines was transmural when the CS was open. Overall, RF applications were sufficient to create lesion depth up to 76%±18% of the left atrial wall.

No device related adverse events were seen during the procedures. An epicardial hemorrhagic pericarditis was seen in the first animal (compatible with previous myocarditis, and unlikely to be related to the device). These finding were not seen in the subsequent eight (8) animals. The lungs were normal and the CS was normal upon post mortem examination in all animals. No blood clots were observed. The balloon was intact in all devices tested.

Example Set B

The following numbered sentences are intended as illustrative and not limiting as to the subject matter contemplated per this disclosure and to provide some context to those of skill in the art as to the procedures contemplated herein.

1. A method for ablating a portion of myocardium located adjacent to a coronary vessel of a heart, said method comprising:

inserting an occlusion catheter having an expandable film of material around a distal portion thereof into a coronary vessel of a heart, wherein said occlusion catheter includes a reinforcing layer of material within at least a portion of a shaft of the catheter near a proximal end of the expandable film of material;

one of at least partially and fully occluding blood flow within the vessel using the occlusion catheter with the expandable film of material in an expanded state disposed in contact with one of the ostium of the vessel and an inner surface of the vessel;

inserting an ablation catheter into a chamber of the heart;
positioning the ablation catheter against a portion of myocardium adjacent the vessel; and
ablating the portion of the myocardium adjacent the vessel while the vessel is at least partially occluded.

2. A method in accordance with example 1, wherein inserting an occlusion catheter comprises inserting a distal end portion of the occlusion catheter distal to the expandable film of material into a portion of a vein branching from a CS, and wherein the distal end portion is either comprised of a material having a softer elasticity modulus relative to proximal portions of the occlusion catheter or is free of the reinforcing layer of material.

3. A method in accordance with example 2, wherein occluding the vessel comprises inflating a balloon on the occlusion catheter to occlude the vessel, after the occlusion catheter has been inserted into the portion of the vein.

4. A method in accordance with example 1, wherein inserting an ablation catheter comprises inserting the ablation catheter through a portion of interatrial septal wall and into a left atrium of the heart.

5. A method in accordance with example 1, wherein positioning the ablation catheter comprises positioning a distal portion of the ablation catheter proximate the vessel.

6. A method in accordance with example 1, wherein ablating a portion of the myocardium comprises creating a mitral isthmus ablation line.

7. A method in accordance with example 1, wherein ablating a portion of the myocardium comprises creating a transmural lesion in a region between the mitral annulus and the left inferior pulmonary vein ostium.

8. A method in accordance with example 1, further comprising a temperature sensor coupled to the occlusion catheter for sensing temperatures of adjacent tissues.

9. A method in accordance with example 1, further comprising utilizing the occlusion catheter to determine whether errant electrical signals are present in the myocardium.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural or method elements that do not differ from the literal language of the claims, or if they include equivalent structural or method elements with insubstantial differences from the literal languages of the claims.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements, As such, joinder references do not necessarily infer that two elements are directly connected and in fixed relation to each other. [0098] It is intended that all matter contained in the above description or shown in the accompanying drawings shall be interpreted as illustrative only and not limiting. Changes in detail or structure may be made without departing from the spirit of the invention as defined in the appended claims.

We claim:

1. A method for creating a bi-directional mitral isthmus block in a heart, said method comprising:
inserting an occlusion catheter having a balloon and at least one of a first electrode and a first coil on a distal portion of the occlusion catheter into a coronary sinus (CS) of the heart, the at least one of the first electrode and the first coil coupled with an electroanatomical localization system comprising a computer system;
expanding the balloon to anchor the at least one of the first electrode and the first coil in the CS;
inserting an ablation catheter having at least one of a second electrode and a second coil into a left atrium of the heart, the at least one of the second electrode and the second coil is coupled with the electroanatomical localization system and is configured to provide a non-transitory signal for the computer system indicative of a position of the at least one of the second electrode and the second coil;
ablating, while the balloon is expanded and anchored in the CS, a portion of a myocardium to create the bi-directional isthmus block with the ablation catheter;
selecting, by the computer system, the at least one of the first electrode and the first coil as a reference node; and
monitoring, by the computer system, a location of the ablation catheter by measuring the non-transitory signal with reference to the reference node.

2. A system comprising:
a first medical device comprising:
a catheter body having a distal portion and a bend located over a part of the distal portion;
a balloon located proximal of the bend and configured to contact an inner surface of a coronary sinus (CS) when positioned therewithin;
a plurality of marker bands positioned on the catheter body; and
at least one of a plurality of electrodes and a coil positioned on the catheter body; and
an electroanatomical localization system comprising a computer system coupled with the first medical device, the computer system configured to select one of: (a) the plurality of marker bands, or (b) one of the at least one of a plurality of electrodes, and the coil as a reference node and to determine a position of a second medical device with reference to the reference node,
wherein at least one of the balloon and the catheter body includes at least one passageway extending from a first opening to a second opening in the balloon, the at least one passageway having a longitudinal axis centered in the at least one passageway different from an axis centered in a longitudinal lumen of the first medical device, the at least one passageway configured to permit blood to flow through the at least one passageway while the balloon is inflated and contacting an inner surface of the CS and both the first and second opening are within a blood vessel.

3. The system of claim 2 wherein at least one of the plurality of marker bands is located within the balloon.

4. The system of claim 2 further comprising at least one sensor attached to one of an interior surface of the balloon and an exterior surface of the balloon.

5. The system of claim 4 wherein the at least one sensor is a temperature sensor configured to detect a temperature of adjacent tissue.

6. The system of claim 2 further comprising at least one sensor positioned within the balloon and spaced apart from an interior surface of the balloon.

7. The system of claim 2 wherein an angle of the bend is between 30 and 60 degrees.

8. The system of claim 2, wherein the electroanatomical localization system comprises one of an impedance-, a magnetic-, and a current-based electroanatomical system.

9. The system of claim 2 wherein the balloon has one of a substantially cylindrical shape and a tapered shape.

10. The system of claim 2, wherein the electroanatomical localization system comprises an impedance-based system, and said electroanatomical localization system is configured to determine the position of the second medical device by measuring a voltage between an electrode coupled to the second medical device and an electrode of the plurality of electrodes.

* * * * *